(12) United States Patent
Corda et al.

(10) Patent No.: US 7,625,883 B1
(45) Date of Patent: Dec. 1, 2009

(54) GLYCEROPHOSPHOINOSITOL DERIVATIVES AS MODULATORS OF CYTOSOLIC A2 PHOSPHOLIPASE

(75) Inventors: Daniela Corda, Fossagesia (IT); Roberto Dal Toso, Sonizzo (IT); Giovanna Bonvento, Frassinelle Polesine (IT); Gabriele Marcolongo, Due Carrare (IT); Renzo Dal Monte, Brendola (IT)

(73) Assignee: I.R.B. Istituto di Ricerche Biotechnologiche S.R.L., Atalvilla Vicentina (IT)

( * ) Notice: Subject to any disclaimer, the term of this patent is extended or adjusted under 35 U.S.C. 154(b) by 417 days.

(21) Appl. No.: 10/415,881

(22) PCT Filed: Nov. 7, 2000

(86) PCT No.: PCT/IT00/00447

§ 371 (c)(1),
(2), (4) Date: Jan. 26, 2004

(87) PCT Pub. No.: WO02/38575

PCT Pub. Date: May 16, 2002

(51) Int. Cl.
*A61K 31/6615* (2006.01)
*C07F 9/02* (2006.01)

(52) U.S. Cl. .......................... 514/148; 554/79
(58) Field of Classification Search .................. 554/79; 514/148

See application file for complete search history.

(56) References Cited

FOREIGN PATENT DOCUMENTS

| EP | 0 100 499 | 2/1984 |
|---|---|---|
| EP | 0 496 474 A2 | 7/1992 |
| FR | 2 517 310 | 6/1983 |
| WO | WO 91 06301 A | 5/1991 |
| WO | WO 91/12256 | 8/1991 |
| WO | WO 95 05479 A | 2/1995 |
| WO | WO 97/48381 | 12/1997 |

OTHER PUBLICATIONS

Young et al. "Total Synthesis of the Four Stereoisomers of Dihexadecanoyl Phophatidylinositol and the Substrate Stereospecificity of Human Erythrocyte Membrane Phosphatidylinositol 4-Kinase" J. Med. Chem. 1990, vol. 33, pp. 641-646.*

Burke et al. "Cooperativity and Binding in the Mechanism of Cytosolic Phospholipase A2" Biochemistry, 1995, vol. 34, pp. 15165-15174.*

Berrie, C.P. et al, "Membrane transport and in vitro metabolism of the Ras cascade messenger, glycerophosphoinositol 4-phosphate" European Journal of Biochemistry, vol. 266, No. 2, Dec. 1999 pp. 413-419, XP001011370.

Brown, D.M. et al., "Phospholipids. Part V. The Hydrolysis of Glycerol 1-esters of myoinositol 1- and 2- Phosphate," Journal of The Chemical Society, Nov. 1959, pp. 3547-3552, XP002171609.

Chemical Abstracts, vol. 075, No. 13, Sep. 27, 1971, Columbus, OH, US; abstract No. 088863, Klyashchitskii B. A. et al, Klyashchitskii B. A. et al., "Derivatives of asymmetrically substituted myoinositol. VI., Synthesis of 2, 3, 4, 5, 6- and 1, 2, 4, 5, 6-penta-O-benzyl-sn-glyceryl-phosphoryl)-sn-myo-inositol" XP002171809.

Corda D. et al., "Glycerophosphoinositols as potential markers of Ras-induced transformation and novel second messengers," Anticancer Research, vol. 16, No. 3B, May 1996, pp. 1341-1350, XP001011369.

Morisaki, N. et al., "Phosphorylation of Unnatural Phosphatidylinositols with Phosphatidylinositol 3-Kinase" Tetrahedron, NL, Elsevier Science Publishers, Amsterdam, vol. 56, No. 17, Apr. 2000, pp. 2603-2614, XP0041974757.

Shirai, R. et al., "The Structural requirement of Phosphatidylinositols as substrate of Phosphatidylinositol 3- Kinase," Tetrahedron Letters, NL, Elsevier Science Publishers, Amsterdam, vol. 40, No. 9, Feb. 26, 1999, pp. 1693-1696, XP004157168.

Shvets V.I. et al., "Rosolution of Asymmetrically Substituted Myoinositols into Optical Antipodes," Tetrahedron., vol. 29, No. 2, 1973, pp. 331-340, XP002171610.

Young, R.C. et al., "Total synthesis of the four stereoisomers of dihexadecanoyl phosphatidylinositol and the substrate stereospecificity of human erythrocyte membrane phosphatidylinositol 4-kinase," Journal of Medicinal Chemistry, vol. 33, No. 2, Feb. 1990 pp. 641-646, XP002171611.

Armandi-Burgermeister, E., et al. Suppression of cytokine synthesis integrin expression and chronic inflammation by inhibitors of cytosolic phospholipase A2, European Journal of Pharmacology, May 20, 1997, pp. 237-250, vol. 326, Elsevier Science B.V.

Berrie, C.P., et al., "Glycerophosphoinositol-4-phosphate in intracellular signalling" in *Bioactive Lipids*, Vanderbock, Y.Y.. ed., 1998, pp. 229-237 Plenum Publishing.

* cited by examiner

*Primary Examiner*—Rebecca L Anderson
*Assistant Examiner*—Joseph R Kosack
(74) *Attorney, Agent, or Firm*—Kalow & Springut LLP

(57) ABSTRACT

Optionally O-substituted glycero-phosphoinositol derivatives, their analogues and their salts wherein the substitutents: R'1, R'2, R2, R3, R4, R5, R6 have the described meaning, their synthesis and their pharmacological effect as modulators of the activation or over-stimulation of cPLA2.

19 Claims, No Drawings

GLYCEROPHOSPHOINOSITOL DERIVATIVES AS MODULATORS OF CYTOSOLIC A2 PHOSPHOLIPASE

PARENT APPLICATION

The present application is a national-stage application under 35 USC § 371 of international PCT application PCT/IT00/00447, filed 7 Nov. 2000.

FIELD OF THE INVENTION

The present invention regards the use of glycerophosphoinositols for the preparation of a therapeutical drug for the inhibition of the release of arachidonic acid, new derivatives with glycerophosphoinositolic structure and their preparation. Phospholipases are enzymes that catalyze the hydrolysis of membrane phospholipids and are classified according the type of chemical bond involved, in phospholipase A1, A2, B, C, D.

BACKGROUND ART

In mammals, the mobilization of arachidonic acid from the sn2 ester bond of phospholipids is greatly due to the activation of cytosolic phospholipase A2 (cPLA2) following the receptor activation induced by a number of agonists including hormones, neurotransmitters, neuropeptides and growth factors.

Considering the mechanism of PLA2 activation via the agonist-receptor interaction, the G-proteins have been proposed to mediate the receptor induced activation through two distinct mechanisms: (i) direct interaction with the PLA2, since it is well known that the treatment with pertussis toxin reduces its enzymatic activity; or (ii) indirectly mediated through phospholipase C (PLC) activation, phosphorilation and activation of the PLA2 by the Mitogen Activated Protein Kinases (MAPK).

Two isoforms of the phospholipase A2 have been identified in mammals, a 14 kDa secretory form and a 85 kDa cytosolic form (cPLA2) which do not share amino acid sequence homology and differ in their catalytic and regulatory mechanisms. The cytosolic phospholipase A2 is located in the cytosol of quiescent cells, for example platelets and leucocytes: lipopolisaccharide, thrombin or cytokines (for example Interleukin 1β), Tumor Necrosis Factor α, but also neuropeptides such as tachikinins, bradikinins or neurotransmitters such as purines, particularly ATP, and serotoninergic, adrenergic and muscarinic agonists activate the enzyme leading to an increase of the intracellular calcium levels and a rapid phosphorilation of the enzyme by protein Kinase C and a subsequent translocation to the plasma membrane where it binds to the phospholipid substrate. These mediators also induce the de novo synthesis of the enzyme (E. Armandi-Burgermeister, U. Tibes, B. M. Kaiser, W. G. Friebe, W. V. Scheuer, "Suppression of cytokine synthesis, integrin expression and chronic inflammation by inhibitors of cytosolic phospholipase A2" Europ. J. Pharmacol., 326 (1997) 237-250).

The tight intermodulation of the G protein, PKC, cPLA2 systems and the involvement of the cPLA2 in the production of lipid and lysolipid mediators (Glycerophosphoinositol-4-phosphate in intracellular signaling "C. P. Berrie, M. Falasca, A. Carvelli, C. Iurisci and D. Corda, in Bioactive Lipids, Vanderbock YY/ed. Plenum Publishing Corporation New York, 1998) make the PLA2 a potentially important pharmacological target.

The applicant has now originally found that a substance generated concomitantly with the release of arachidonic acid, that is L-α-glycero-phospho-D-mio-inositol (GPI), is an autacoid and, furthermore, its potassium, calcium and zinc salts and other new derivatives and analogues obtained by chemical semisynthesis and having the general formula (I) subsequently described, exert a potent inhibitory effect on the release of arachidonic acid via a negative modulation of the PLA2 in vitro activation and can be effectively used for the treatment of pathologies mediated by the activation of PLA2 as following described.

SUMMARY OF THE INVENTION

Object of the present invention are the derivatives and analogues of the glycero-phospho-D-mio-inositol optionally O-substituted in positions 2,3,4,5,6 or 1' and 2', characterized by the following general formula:

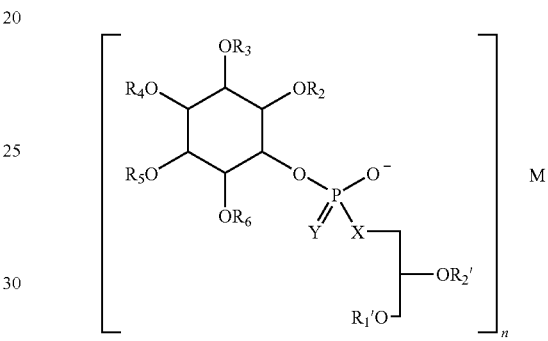

where R'1, R'2, R2, R3, R4, R5, R6, equal or different between each other, can be either H, or C(O)A or B where the meaning of A, B, X, Y and M are subsequently detailed.

The present invention relates also to the use of L-α-glycero-phospho-D-mio-inositol (GPI) and its salts, particularly with metal alkaline or earth alkaline, particularly calcium, and with zinc together with the new derivatives according to formula (I) for the preparation of a medicament for the treatment of pathologies mediated by the activation or over activation of the PLA2.

The present invention furthermore relates to pharmaceutical compositions which contain as the active ingredient at least one of the derivatives of formula (I) associated with adequate excipients for the treatment of pathologies mediated by the activation or over stimulation of the PLA2, particularly, septic shock and viral and bacterial infections, pathologies of the respiratory apparatus, such as acute pulmonary damage including new-born pathologies, chronic obstructive bronchopathies including asthma; dermatologic pathologies such as psoriasis, seborrheic dermatitis, atopic dermatitis and more generally skin dis-reactivity involving also the oxidative stress following UV damage; damages to the gingival tissue due also to bacterial infections; intestinal ischemia; articular pathologies such as arthritis and arthrosis, including rheumatoid arthritis; opthalmologic pathologies, headaches, cardiovascular pathologies associated with vascular remodeling, kidney pathologies and any pathology associated with the over stimulation of PLA2 enzyme even mediated by the activation of specific receptors and growth factors such as EGF, NGF or of tachikinins such as the NK receptors, or of purines (for example ATP) such as the P2Y, or of neuropeptides such as bombesin or other receptors coupled with G proteins which activate PLA2; tumor pathologies, such as the prostate and kidney carcinoma, or in any way dependent on the activation of the PLA2, pain and iperalgesia, pathologies of the Central and Peripheral Nervous System and pathologies depending on the sphyngomielin cycle, including the hereditary forms such as the Hermansky-Pudlak and the Nieman-Pick syndromes; pathologies associated with damage to the barrier between vessel and nervous system such as the perineurium of the nerves and the blood brain barrier, for example neuronal edema, stroke, cerebral edema and hemorrhage, TIA (Transient Ischemic Attack); Alzheimer's disease or behavioral disorders such as schizophrenia; dis-metabolic pathologies such as diabetes; pancreatitis, pathologies related to food intake disorders such as bulimia, anorexia, cachessia, obesity, depression.

The characterization and the advantages of the derivatives and analogues of glycero-phospho-D-mio-inositol according to formula (I) as agents capable to negatively modulate the over stimulation of the phospholipase A2, and particularly its cytosolic isoform (cPLA2), with subsequent inhibition of the release of arachidonic acid and of its metabolites, will be described in detail in the following sections.

DETAILED DESCRIPTION OF THE INVENTION

The invention regards the compounds according to the general formula (I)

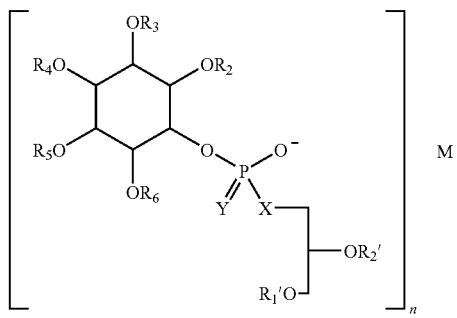

their enantiomers, diastereoisomers, racemes, their mixtures, their hydrates and solvates, wherein:

I) R', R2', R2, R3, R4, R5, R6 can be equal or different among each other being a) H or a group C(O)A, acylic residue of mono-carboxylic acid or emiacylic residue of di-carboxylic acid, where A can be: an alkyl radical saturated or unsaturated having from 1 to 4 double bond, straight or branched, or an alkyl or alkenyl group mono o poli-cyclic, or an aryl, arylalkyl or heterocyclic group having one or more heteroatoms; these groups can be optionally substituted with one or more groups selected among keto, hydroxy, acylamido, halogen, mercapto, alkylthio or alkyldithio, —COOH and where these —COOH are optionally neutralized to form a —COOM salt wherein M has the same meaning described at point (II); or a group B wherein B is an alkyl group saturated or unsaturated with from 1 to 6 double bonds, straight or branched; or an alkyl or alkenyl group mono- or poly-cyclic or an aryl, alkylaryl group or heterocycle group having one or more heteroatoms; these groups are optionally substituted with one or more groups selected among keto, hydroxy, acylamido, halogen, mercapto, alkylthio or alkyldithio, —COOH and these —COOH are optionally neutralized to form a —COOM salt wherein M has the same meaning described at point (II)

((II) M is the cation of an inorganic element pharmacologically acceptable, or a cation of an organic base pharmacologically acceptable having valence n+ wherein n has the meaning described in the following point (III);

(III) n is equal to 1 or 2 or 3;

(IV) X e Y identical or different among each other are O or S;

and wherein, when Y is S, the compounds according to formula (I) include also the respective non-neutralized compounds.

More Detailed

Description of A:

i) when A is an alkyl group it is preferably saturated or mono-unsaturated and preferably has from 1 to 8 carbon atoms, and preferably from 2 to 6.

ii) when A is an alkyl or alkenil group mono-o poly-cyclic it has preferably from 5 to 30 carbon atoms, more preferably from 6 to 24 carbon atoms.

when A is an aryl, arylalkyl or heterocycle group having one or more heteroatoms, it has preferably from 4 to 15 carbon atoms and more preferably from 4 to 8. The heteroatoms are from 1 to 5 and preferably from 1 to 3. They are N, O or S, preferably N. These heteroatoms N can be optionally neutralized to form a salt with a pharmacologically acceptable organic or inorganic acid.

Description of B:

i) when B is an alkyl it is preferably saturated or mono-unsaturated. Preferably it has from 1 to 8 carbon atoms and more preferably from 2 to 6 carbon atoms.

ii) when B is an alkyl or alkenyl radical, mono- or poly-cyclic, it has preferably from 5 to 30 carbon atoms, more preferably from 6 to 24 carbon atoms.

when B is an aryl, arylalkyl or heterocycle having one or more heteroatoms, it has preferably from 5 to 15 carbon atoms and more preferably from 5 to 8. The heteroatoms are preferably from 1 to 5 and more preferably from 1 to 3. They are N, O or S, preferably N. These heteroatoms N can be optionally neutralized to form a salt with a pharmacologically acceptable organic or inorganic acid.

Description of M:

i) when M is the cation of a pharmacologically acceptable inorganic element, it is preferably selected among sodium, lithium, potassium, magnesium, calcium, zinc, iron, selenium, chromium, copper.

ii) when M is the cation of a pharmacologically acceptable organic base, it is preferably a mono-, di-, tri-o tetra-alkylammonium, more preferably N-(2-hydroxyethyl)-dimethylammonium, a cation of choline or of an amino acid, preferably lysine or arginine or a cation of mono-, di-, tri and tetra-peptides preferably carnosine or cations of xanthine base and, preferably, caffeine.

The term acylamino means preferably a acetylamino group.

The term alkoxy means preferably methoxy-, ethoxy or allyloxy groups.

The term halogen means preferably chloride, fluoride, bromide or iodide.

The term arylalkyl radical means preferably a C7-C9-arylalkyl group and more preferably a benzyl.

The term aryl radical means preferably a C6-C12-aryle, preferably a phenyl.

The term heterocycle means preferably the radical of a saturated, unsaturated or aromatic heterocycle, with a 5 or 6 atom-ring.

The term cycloalkyl or cycloalkylenic radical means preferably a ring mono- or poly-cyclic having preferably from 5 to 30 carbon atoms, more preferably from 6 to 24 carbon atoms.

X and Y identical or different with each other are O or S and are preferably equal each other and preferably equal to O.

A further object of the present invention is the use of the compounds of formula (I) and of the related non-salified products for the treatment of pathologies mediated by the activation or over-stimulation of cPLA2, with particular regard to the pathologies previously listed.

Preparation of the Compounds of the Invention

The preparation of the compounds of the present invention is carried out preferably, but not limited to, starting from L-α-glycero-phospho-D-myo-inositol (GPI); the homologous of GPI containing sulphur atoms, glycerophosphothioinositols are prepared according to the methods described in the following examples starting from commercially available intermediates, or prepared according to simple methods reported in the literature. GPI is a known substance available as commercial product in form of potassium salt. GPI in aqueous solution at room temperature is stable only at pH values near to the neutrality. At different pH value the molecule is subjected to hydrolysis reactions and is degraded. The following methods described herein for the preparation of new salts of GPI, have been shown efficient in maintaining the stability of the structure of GPI.

The following new GPI salts herein described have been prepared mainly starting from potassium salt, nevertheless the following methods herein described are suitable for the preparation of any of the new derivatives starting from different salts wherever required by industrial opportunity.

General Methods for the Preparation of New L-α-glycero-phospho-D-myo-inositol Salts (GPI).

Method I

The general method for the preparation of inorganic and organic salts of L-α-glycero-phospho-D-mio-inositol (GPI) is according to U.S. Pat. No. 5,306,840 and briefly it will be as follows: solubilization of the starting salt in water or mixture of water and mixture of water and an organic solvent and then application to a column of cationic exchange resin, generated as H+ form at temperature of 4° C. The solution of GPI acid form eluted is collected and kept at 0-4° C. then neutralised mole to mole with a base of a cation organic or inorganic biologically acceptable to give the related salt. The solution can be used as it is for the subsequent operations of formulation or it can be dried under vacuum by lyophilization or spray-dryer to obtain the salt of GPI pure and dry as a solid.

The general method for the preparation of alkyl or acyl derivatives on —OH group(s) of L-α-glycero-phospho-D-mio-inositol (GPI) is generally performed starting from a GPI salt prepared according to the U.S. Pat. No. 5,306,840, generally the potassium salt or a salt with quaternary ammonium, preferably terbutylammonium in an organic solvent pure or mixture of organic solvents or mixture of an organic solvent with water at a concentration between 10 to 500 mg/ml and preferably 50 to 200 mg/ml. Among the organic solvents the following are preferred: acetone, 2-butanone, methylisobutylketone, dimethylsulfoxide, sulfolane, dimethylformamide, dimethylacetylamide, n-methyl-2-pyrrolidone, pyridine, tetrahydrofurano, methyltetrahydrofurano, acetonitrile, dimethoxyethane, diethylether, terbutylmethylether, ethyl acetate, chloroform, dichloromethane, 1,1,1-trichloroethane, methanol, ethanol, 2-propanol, butanol. The reactions are performed at temperature between −30° C. and +120° C. and preferably +5° C. to +40° C. over a time from 15 minutes to 48 hours and preferably between 1 hour and 15 hours.

To insert —C(O)A groups, acylic groups of monocarboxylic acids or emiacylic group of dicarboxylic acid as defined at point I of the detailed description, GPI reacts with activated derivatives of the above acid and preferably chloride, bromide, mixed anhydrides, cyclic anhydrides, activated esters such as p-nitrophenylesters, succinimidylesters, acylimidazole, O-acylisoureas and preferably but no limitatively in presence of an organic or inorganic bases. These bases are preferably carbonate, bicarbonate, oxide, hydroxide, hydrides and alcoholates of alkaline or earth alkaline metals and preferably lithium, sodium, potassium, magnesium, calcium, trimethylammine, triethylammine, tributylammine, tetramethylammonium hydroxide, tetrabutylammonium hydroxide, pyridine or picoline.

To insert B groups as defined at point (I) of the detailed description, GPI reacts with activated derivatives of formula Z-B wherein Z is an alogen and preferably chloride, bromide or iodide, or an alkylsulfonate group and preferably methanesulfonate, benzenesulfonate, p-toluenesulfonate o trifluoromethansulfonate. The reaction of GPI with Z-B is performed preferably but non limitatively in presence of an inorganic or organic base. These bases are preferably carbonate, bicarbonate, oxide, hydroxide, iodide and alcoholates of alkaline or earth alkaline metals and preferably lithium, sodium, potassium, magnesium, calcium, trimethylamine, triethylamine, tributylamine, tetramethylammonium hydroxide, tetrabutylammonium hydroxide, pyridine or picoline.

In the same manner are prepared alkyl or acyl derivatives of the homologues of GPI containing S atoms: the glycerophosphotioinositols.

Example 1

Preparation of Magnesium Salt of L-α-glycero-phospho-D-mio-inositol 3.7 g of GPI potassium salt (10 mmoles) are dissolved in 35 ml of distilled water. The solution is cooled at 4° C. and applied to a column containing 15 ml of cationic exchange sulphonic resin generated in H+ form and thermostated at 4° C. The column is then eluted with 15 ml of distilled water and the eluate is collected at 4° C., flowed with nitrogen stream and neutralised with 0.292 g of magnesium hydroxide. The obtained solution is filtered, frozen and vacuum dried.

The reaction yields 98%.

The chemical-physical characteristics of the product L-α-glycero-phospho-D-mio-inositol magnesium salt are:

| | |
|---|---|
| Appearance | white powder |
| molecular formula | $(C_9H_{18}O_{11}P)_2$ Mg |
| molecular weight | 690.71 |
| elemental analysis | C = 31.3%; H = 5.25%; O = 50.96%, P = 8.97%, g = 3.52% |
| solubility in organic solvents | slightly soluble in organic solvents |
| solubility in water | >10 mg/ml |
| TLC | 100 mcg applied to a silica gel glass; developing solvent A chloroform/ |

Example 2

Preparation of Calcium Salt of L-α-glycero-phospho-D-mio-inositol 3.7 g of GPI potassium salt (10 mmoles) are dissolved in 35 ml of distilled water. The solution is cooled at 4° C. and applied to in a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 0.370 g of calcium hydroxide. The obtained solution is filtered, frozen and vacuum dried.

The reaction yields 98%.

The chemical-physical characteristics of the product L-α-glycero-phospho-D-mio-inositol magnesium salt are:

| | |
|---|---|
| Appearance | white powder |
| molecular formula | $(C_9H_{18}O_{11}P)_2$ Ca |
| molecular weight | 706.48 |
| elemental analysis | C = 30.6%; H = 5.14%; O = 49.82%, P = 8.77%, Ca = 5.67% |
| solubility in organic solvents | slightly soluble in organic solvents |
| solubility in water | >10 mg/ml |
| TLC | 100 mcg applied to a silica gel glass; developing solvent A chloroform/methanol/water 3:3:1 developing solvent B acetonitrile/water 3:1, spray $KMnO_4$ basic - complying with the standard of GPI no degradation product is observed. |

Example 3

Preparation of Zinc Salt of L-α-glycero-phospho-D-mio-inositol 3.7 g of GPI potassium salt (10 mmoles) are dissolved in 35 ml of distilled water. The solution is cooled at 4° C. and applied to a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 0.54 g zinc carbonate basic. The obtained solution is filtered, frozen and vacuum dried.

The reaction yields 99%.

The chemical-physical characteristics of the product L-α-glycero-phospho-D-mio-inositol zinc salt are:

| | |
|---|---|
| Appearance | white powder |
| molecular formula | $(C_9H_{18}O_{11}P)_2$ Zn |
| molecular weight | 731.78 |
| elemental analysis | C = 29.54%; H = 4.96%; O = 48.1%, P = 8.47%, Zn = 8.93% |
| solubility in organic solvents | slightly soluble in organic solvents |
| solubility in water | >10 mg/ml |
| TLC | 100 mcg applied to a on silica gel plate; developing solvent A chloroform/methanol/water 3:3:1 developing solvent B acetonitrile/water 3:1, spray $KMnO_4$ basic - complying with the standard of GPI no degradation product is observed. |

Example 4

Preparation of Sodium Salt of L-α-glycero-phospho-D-myo-inositol 3.7 g of GPI potassium salt (10 mmoles) are dissolved in 35 ml of distilled water. The solution is cooled at 4° C. and applied to a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 0.53 g sodium carbonate basic. The obtained solution is filtered, frozen and vacuum dried.

The reaction yields 98%.

The chemical-physical characteristics of the product L-α-glycero-phospho-D-mio-inositol sodium salt are:

| | |
|---|---|
| Appearance | white powder |
| molecular formula | $C_9H_{18}O_{11}P$ Na |
| molecular weight | 356.2 |
| elemental analysis | C = 30.35%; H = 5.09%; O = 49.41%, P = 8.70%, Na = 6.45% |
| solubility in organic solvents | slightly soluble in organic solvents |
| solubility in water | >10 mg/ml |
| TLC | 100 mcg applied to a silica gel plate; developing solvent A chloroform/methanol/water 3:3:1; developing solvent B acetonitrile/water 3:1, spray $KMnO_4$ basic - complying with the standard of GPI no degradation product is observed. |

Example 5

Preparation of Choline Salt of L-α-glycero-phospho-D-mio-inositol 3.7 g of GPI potassium salt (10 mmoles) are dissolved in 35 ml of distilled water. The solution is cooled at 4° C. and applied in a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 2.69 g of a solution of choline in methanol 45%. The obtained solution is filtered, frozen and vacuum dried.

The reaction yields 98%.

The chemical-physical characteristics of the product L-α-glycero-phospho-D-mio-inositol choline salt are:

| | |
|---|---|
| Appearance | powder |
| Formula | $C_9H_{18}O_{11}P \cdot C_5H_{14}NO$ |
| molecular formula | $C_{14}H_{32}NO_{12}P$ |
| molecular weight | 437.37 |

Example 6

Preparation of Lysine Salt of L-α-glycero-phospho-D-mio-inositol 3.7 g of GPI potassium salt (10 mmoles) are dissolved in 35 ml of distilled water. The solution is cooled at 4° C. and applied in a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 1.46 g of lysine. The obtained solution is filtered, frozen and vacuum dried.

The reaction yields 99%.

The chemical-physical characteristics of the product L-α-glycero-phospho-D-mio-inositol lysine salt are:

| | |
|---|---|
| Appearance | powder |
| Formula | $C_9H_{19}O_{11}P \cdot C_6H_{14}N_2O_2$ |
| molecular formula | $C_{15}H_{33}N_2O_{13}P$ |
| molecular weight | 480.40 |
| elemental analysis | C = 37.50%; H = 6.92%; N = 5.83%; O = 43.30, P = 6.45% |
| solubility in organic solvents | slightly soluble in organic solvents |
| solubility in water | >10 mg/ml |
| TLC | 100 mcg applied to a silica gel plate; developing solvent A chloroform/methanol/water 3:3:1 developing solvent B acetonitrile/water 3:1, spray $KMnO_4$ basic - complying with the standard of GPI; no degradation product is observed. |

Example 7

Preparation of Arginine Salt of L-α-glycero-phospho-D-mio-inositol 3.7 g of GPI potassium salt (10 mmoles) are dissolved in 35 ml of distilled water. The solution is cooled at 4° C. and applied to a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 1.74 g of arginine. The obtained solution is filtered, frozen and vacuum dried.

The reaction yields 98%.

The chemical-physical characteristics of the product L-α-glycero-phospho-D-myo-inositol arginine salt are:

-continued

| | |
|---|---|
| elemental analysis | C = 38.45%; H = 7.38%; N = 3.20; O = 43.90, P = 7.08% |
| solubility in organic solvents | slightly soluble in organic solvents |
| solubility in water | >10 mg/ml |
| TLC | 100 mcg applied to silica gel plate; developing solvent A chloroform/methanol/water 3:3:1 developing solvent B acetonitrile/water 3:1, spray $KMnO_4$ basic - complying with the standard of GPI; no degradation product is observed. |

| | |
|---|---|
| Appearance | powder |
| Formula | $C_9H_{19}O_{11}P \cdot C_6H_{14}N_4O_2$ |
| molecular formula | $C_{15}H_{33}N_4O_{13}P$ |
| molecular weight | 508.42 |
| Elemental analysis | C = 35.44%; H = 6.54%; N = 11.02%; O = 40.91%; P = 6.09% |
| solubility in organic solvents | slightly soluble in organic solvents |
| solubility in water | >10 mg/ml |
| TLC | 100 mcg applied to a silica gel plate; developing solvent A chloroform/methanol/water 3:3:1 developing solvent B acetonitrile/water 3:1, spray $KMnO_4$ basic - complying with the standard of GPI; no degradation product is observed. |

Example 8

Preparation of Tetrabutylammonium Salt of L-α-glycero-phospho-D-mio-inositol 3.7 g of GPI potassium salt (10 mmoles) are dissolved in 35 ml of distilled water. The solution is cooled at 4° C. and applied to a column containing 15 ml of cationic exchange sulfonic resin generated in H+ form and thermostated at 4° C. The column is then eluted with 15 ml of distilled water and the eluate is collected at 4° C., flowed with nitrogen stream and neutralised with 10 ml of 1M aqueous solution of tetrabutylammonium hydroxide. The obtained solution is filtered, frozen and lyophilised.

The reaction yields 97%.

The L-α-glycero-phospho-D-mio-inositol tetrabutylammonium salt show the following characteristics:

| | |
|---|---|
| Appearance | powder |
| Formula | $C_9H_{18}O_{11}P \cdot C_{16}H_{36}N$ |
| molecular formula | $C_{25}H_{54}NO_{11}P$ |
| molecular weight | 575.69 |
| elemental analysis | C = 52.16%; H = 9.46%; N = 2.43%; O = 30.57%; P = 5.38% |
| solubility in organic solvents | slightly soluble in organic solvents, ≧10 mg/ml in DMF |
| solubility in water | >10 mg/ml |
| TLC | 100 mcg applied to a silica gel plate; developing solvent A chloroform/methanol/water 3:3:1 developing solvent B acetonitrile/water 3:1, spray $KMnO_4$ basic - complying with the standard of GPI; no degradation product is observed. |

Example 9

Preparation of Potassium Salt of L-α-glycero-phospho-D-mio-inositol Peracetilated 5.76 g of GPI tetrabutylammonium salt (10 mmoli) are dissolved in 35 ml of anhydrous DMF. The mixture is cooled at 4° C. under stirring. 15 ml of anhydrous pyridine and 10 ml of acetic anhydride are added slowly, drop by drop, under stirring over 30 minutes. The mixture is brought to room temperature and kept under stirring for 48 hours in anhydrous conditions. The mixture is then dried under vacuum. The residue is suspended in 10 ml of ethanol and 100 mg of KCl and then precipitated by adding 30 ml of diethylether. The obtained residue is suspended with 30 ml of water and 20 g of ice and extracted three times with 30 ml of tetrahydrofuran. The upper layers are collected and dried. The obtained residue is dissolved in 30 ml of ethanol and eluted in a column containing 15 ml of cationic exchange sulfonic resin generated in K+ form. The eluate is evaporated under vacuum and then dried under high vacuum.

The reaction yields 90%.

The chemical-physical characteristics of the product L-α-glycero-phospho-D-mio-inositol potassium salt peracetylated are:

| | |
|---|---|
| Appearance | powder |
| molecular formula | $C_{23}H_{32}O_{18}PK$ |
| molecular weight | 666.58 |
| elemental analysis | C = 41.44%; H = 4.84%; O = 43.21%; P = 4.65%; K = 5.87% |
| solubility in organic solvents | ≧10 mg/ml in DMF and ethanol |

Example 10

Potassium salt of glycerotio-phospho-D-mio-inositol. [—S—P—]

The compound is prepared starting from diacylglycerotio-phosphoril-inositol obtained as described by Kubiak et al. "ACS SYMPOSIUM SERIES" 718, page 180.

1.0 g of diacylglycerotiophosphoryl-inositol is suspended in 10 ml of anhydrous methanol in nitrogen atmosphere. 50 mg of potassium tert-butoxide are added and the mixture is maintained under stirring at 20° C. for 3 hour. 26.7 mg of acetic acid are added, the mixture are dried. The residue is dissolved in 10 ml of cool water and extracted with 10 ml of diethylether. The organic layer is then discarded."

The solution is cooled to 4° C. and applied to a column containing 5 ml of cationic exchange sulfonic resin generated in H+ form and thermostated at 4° C. The column is then eluted with 5 ml of distilled water and the eluate is collected at 4° C., flowed with nitrogen stream and neutralised with 0.1M KOH till pH 7.0. The obtained solution is filtered, frozen and vacuum dried.

The reaction yields 95%.

The chemical-physical characteristics of the product Potassium salt of glycerotio-phospho-D-mio-inositol are:

| | |
|---|---|
| Appearance | powder |
| molecular formula | $C_9H_{18}O_{10}PSK$ |
| molecular weight | 388.38 |
| elemental analysis | C = 27.84%; H = 4.67%; S = 8.25%; O = 41.20%; P = 7.98%; K = 10.07% |
| solubility in organic solvents | slightly soluble in organic solvents |
| solubility in water | ≧10 mg/ml |
| TLC | 100 mcg applied to a silica gel plate; developing solvent A chloroform/methanol/water 3:3:1 developing solvent B acetonitrile/water 3:1, spray $KMnO_4$ basic - Rf = 0.38. |

Example 11

Potassium salt of glycerotio-phosphotio-D-mio-inositol. [—=S]

The synthesis is performed starting from 2,3,4,5,6-penta-O-methoxymethyl-D-mio-inositol described by T. G. Mayer et al Eur. J. Org. Chem. (1998) pag. 291-298.

400 mg of 2,3,4,5,6-penta-O-methoxymethyl-D-mio-inositol (1 mmole) are dissolved in 50 ml of tetrahydrofurane/dichloromethane 1:4 and the mixture is cooled to a −15° C.

70 mg of imidazole and 220 mg of triethylamine are added, then, slowly drop by drop, a solution of 150 mg of phosphorus trichloride in 5 ml of anhydrous dichloromethane.

The obtained mixture is maintained under stirring for 2 hours, then heated to room temperature, added with 10 ml of triethylammonium bicarbonate and stirred for 1 hour. After phase separation, the lower layer is collected, washed two times with 5 ml of cool water, evaporated and dried under high vacuum.

The residue is suspended in 20 ml of anhydrous pyridine then add 200 mg of 5,5-dimethyl-2-oxo-2-chloro-1,2,3-dioxophosphorinane and 132.2 mg of D-α,β-isopropylidenglycerol, then the mixture is stirred at room temperature for 30 min under inert atmosphere. The mixture is dry-evaporated. The residue is suspended in 50 ml of carbon tetrachloride and added with 100 mg of sulphur; stir for 30 min. at room temperature then dry under high vacuum. The residue is solubilized in 20 ml of anhydrous methanol and added with 100 mg of p-toluensulfonic acid. The mixture is heated for two hours to 40° C. then cooled to room temperature, added with 2 ml of water under stirring for 30 min. The mixture is neutralised with ammonium bicarbonate and dried. The residue is purified through preparative chromatography in column of silica gel using as developing solvent a mixture of chloroform/methanol/water 35:25:7. The fractions containing the product are collected and dried under vacuum.

The residue is dissolved in 5 ml of water; the solution is cooled at 4° C. and eluted through a column 5 ml of sulfonic resin, cationic exchange generated in form H+ at 4° C. The column is eluted with 5 ml of distilled water, the eluate is collected at 4° C., flowed with nitrogen stream and neutralised with KOH 0.1 M till pH 7.0. The obtained solution is filtered, frozen and vacuum dried.

The reaction yields 65%.

The chemical-physical characteristics of the product Potassium salt of glycerotio-phosphotio-D-mio-inositol are:

| | |
|---|---|
| Appearance | powder |
| molecular formula | $C_9H_{18}O_{10}PSK$ |
| molecular weight | 388.38 |
| elemental analysis | C = 27.84%; H = 4.67%; S = 8.25%; O = 41.20%; P = 7.98%; K = 10.07% |
| solubility in organic solvents | slightly soluble in organic solvents |
| solubility in water | ≧10 mg/ml |
| TLC | 100 mcg applied to a silica gel plate; developing solvent A chloroform/methanol/water 3:3:1 developing solvent B acetonitrile/water 3:1, spray $KMnO_4$ basic - Rf = 0.35. |

Biological Activity

The compounds have been coded according to the examples and numbered as follows:

| Example | Chemical name |
|---|---|
| Ex. 2 | L-α-glycero-phospho-D-mio-inositol calcium salt |
| Ex. 3 | L-α-glycero-phospho-D-mio-inositol zinc salt |
| Ex. 4 | L-α-glycerol-phospho-D-mio-inositol sodium salt |
| Ex. 4a | L-α-glycero-phospho-D-mio-inositol potassium salt |
| Ex. 5 | L-α-glycero-phospho-D-mio-inositol choline salt |
| Ex. 6 | L-α-glycero-phospho-D-mio-inositol lysine salt |

Compounds from the list above have been variously tested in vitro on cell lines and in vivo in an inflammation model induced with substance P and its peptide P6-1 in mice.

Abbreviations, Reagents and Materials

Hormones: Gibco (Grand Island, NY) (6H-thyrotropin, insulin, transferrin, cortisol, somatostatin, glicil-L-istidil-L-lysin acetate)
Penicillin: Gibco (Grand Island, NY)
Coon's F-12 Medium modified according to Ham: Gibco (Grand Island, NY)
Streptomicin: Gibco (Grand Island, NY)
NaF, $AlCl_3$: Fluka Chem AG (CH)
5,6,8,11,12,14,15-$^3$H(N) arachidonic Acid: Du Pont- NEN (Boston, MA)
BSA Bovine Serum Albumin, Sigma A-3311
Evan's Blue: Sigma E-2129
Formamide: Sigma F-7503
Ethyl Ether: Fluka Chem AG (CH)
PTFE 0, 45 μm Filters: Costar 130662
Substance P, SP: Clinalfa (IT)
SP Carboxy terminal peptide SP6-11 Sigma S-0772
Protein Kinase C, PKC
Phospholipase A2, PLA2
Phospholipase C, PLC
Mitogen activated PK, MAPK Evaluation of the effects of the L-α-glycero-phospho-D-mio-inositol autacoid coded example 4a on the release of arachidonic acid induced by cPLA2 in various cellular systems.

Experimental Models

Cell Cultures

FRTL5, cell line of epithelial cells from rat thyroid grown in culture. Briefly, the cells were cultured in Coon's F12 medium modified according to Ham and supplemented with 5% bovine serum, 20 mM glutamine and a mixture of six hormones. (6H-thyrotropin, insulin, transferring, cortisol, somatostatin, glicil-L-istidil-L-lysine acetate) at 37° C. in a humidified atmosphere in 5% CO2, 95% air medium changed every 3-4 days.

Swiss 3T3 Fibroblasts

The cultures are stimulated to release arachidonic acid using various stimuli:

cPLA2-dependent mechanism, for example ATP, mastoparan, bombesin;

cPLA2-independent mechanism, for example Ca2+ ionophore, ionomicin.

Test

Release of Arachidonic Acid

The cells are initially incubated with various concentrations of the compound under examination for 60 minutes or with a predefined concentration of 100 μM for various time intervals (15-180 minutes), washed two times with HBSS (Hank's Balanced Salt Solution, in the presence of Ca2+ and Mg2+ ions) added with 10 mM Hepes and 0.2% BSA—in absence of free fatty acids, pH 7.4 and stimulated with 100 μM ATP in the described buffer for 10 minutes at 37° C. The supernatant was collected in scintillation cuvettes for determination. The results are expressed as a percentage of the total release of [3H]-arachidonic acid.

Results

The compound under evaluation coded as example 4a has been shown to reduce in a time and concentration dependent manner the release of arachidonic acid induced by the activation of the cPLA2 in all the cellular systems in which the test has been performed (Table 1, 2, 3, 4, 5)

The compounds coded as example 3 and example 4 show a more potent effect (data not shown).

On the contrary, compound example 4a does not induce reduction of the release of arachidonic acid induced by stimuli not related to cPLA2, such as calcium ionophore (Table 6).

All together, data show that the compound of example 4a and that the compounds of example 3 and example 4 (data not reported) are able to limit the release of arachidonic acid according to a mechanism specifically mediated by the negative regulation of the activating pathway of the cytosolic cPLA2, in other words of the main pathway involved in the mobilization of arachidonic acid.

TABLE 1

Time-course of the inhibition of the release of arachidonic acid in the presence of the compound of example 4a in FRTL5 cells stimulated with ATP.

| Time Minutes of preincubation | release of [$^3$H]-arachidonic acid % inhibition |
|---|---|
| 15 | 30 ± 4 |
| 30 | 42 ± 5 |
| 60 | 70 ± 4 |
| 90 | 72 ± 5 |
| 120 | 71 ± 6 |
| 180 | 92 ± 9 |

Preloaded cells are incubated with 100 μM of compound of the Example 4a for different time intervals and then stimulated with ATP (100 μM) for 10 minutes. The results are expressed as the mean±SE of two points in 3 separate experiments. The stimulation of control cells was generally 4-5 times the basal value in the corresponding intervals.

TABLE 2

The compound of example 4a induces a inhibition of the release of arachidonic acid from FRTL5 cells stimulated with ATP.

| Concentration (μM) | Release of [$^3$H]-arachidonic acid % inhibition |
|---|---|
| 0.005 | 10 ± 2 |
| 0.01 | 35 ± 5 |
| 0.1 | 41 ± 2 |
| 1.0 | 52 ± 3 |
| 10 | 60 ± 8 |
| 50 | 70 ± 4 |
| 100 | 92 ± 2 |

Preloaded cells were pre-incubated with various concentrations of the Example 4a for 60 minutes and then stimulated with 100 μM ATP for 10 minutes. The results are expressed as the mean±SE of two points in 3 separate experiments.

TABLE 3

The compound of the Example 4a inhibits the release of [$^3$H]-arachidonic acid from Swiss 3T3 fibroblasts stimulated with ATP.

| Treatment (concentration μM) | Release of [$^3$H]-arachidonic acid % basal |
|---|---|
| ATP | 149 ± 11 |
| Example 4a (50) | 80 ± 9 |
| Example 4a (100) | 70 ± 4 |

Preloaded cells were pre-incubated with various concentrations of the Example 4a for 60 minutes and then stimulated with 100 μM ATP for 10 minutes. The results are expressed as the mean±SE of two points in 3 separate experiments.

TABLE 4

The compound of Example 4a reduces the mastoparan-dependent release of [$^3$H]-arachidonic acid in Swiss 3T3 fibroblasts

| Treatment (Concentration μM) | Release of [$^3$H]-arachidonic acid % basal |
|---|---|
| Mastoparan | 150 ± 12 |
| Example 4a (50) | 90 ± 3 |
| Example 4a (100) | 80 ± 4 |

Preloaded radioactively labeled cells were pre-incubated with various concentrations of the Example 4a for 60 minutes and then stimulated with 100 μM mastoparan for 10 minutes. The results are expressed as the mean±SE of two points in 3 separate experiments.

TABLE 5

The compound of the example 4a reduces the bombesin-dependent release of [$^3$H]-arachidonic acid in Swiss 3T3 fibroblasts.

| Treatment (Concentration μM) | Release of [$^3$H]-arachidonic acid % basal |
|---|---|
| Bombesin | 170 ± 14 |
| Example 4a (50) | 120 ± 3 |
| Example 4a (100) | 90 ± 4 |

Preloaded cells were pre-incubated with various concentrations of the Example 4a for 60 minutes and then stimulated with bombesin for 10 minutes. The results are expressed as the mean±SE of two points in 3 separate experiments.

TABLE 6

Compound of the example 4a does not inhibit the release of the [$^3$H]-arachidonic acid induced by ionomicin in FRTL5 cells.

| Treatment (Concentration μM) | Release of [$^3$H]-arachidonic acid |
|---|---|
| Ionomicin | 320 ± 5 |
| Example 4a (50) | 720 ± 30 |
| Example 4a (100) | 450 ± 14 |

Preloaded cells were pre-incubated with various concentrations of the Example 4a for 60 minutes and then stimulated with 10 μM ionomicin for 30 minutes. The results are expressed as the mean±SE of two points in 3 separate experiments.

Evaluation of the protective activity on the local inflammation induced by the peptide P6-11 of substance P versus Substance P.

Experimental Model

Balb/c mice of female gender, of about 20-22 g, maintained in normal conditions light/dark cycles and fed "ad libitum", are anaesthetized by exposure to a ethyl-ether saturated atmosphere. The animals are then divided in 4 groups of 10 animals each.

The capillary permeability is induced by means of a subcutaneous injection into the left ear pinna of substance P (1 pmole/3 μl) or of its peptide fragment P6-11 (1 pmole/3 μl); the control received an injection of saline solution (Mazzari et al. Eur. J. Pharm. 1996).

Plasma Extravasation in the Ear Pinna of the Mouse.

The mice receive an endovenous injection of Evan's Blue (100 mg/kg) immediately after the substance P or the P6-11 peptide and were sacrificed two hours later. The dye was then extracted by an homogenization (Polytron homogenizer) of the injected ear pinna in 2 ml of formammide. The homogenized tissue was then incubated at 50° C. for 2 hours. The plasma extravasation was measured as optical density of the Evan's Blue at 620 nm (A620), according to the method of Saria and Lunberg (1983).

Solubilization and Administration of the Compounds

The compounds described in the examples have been solubilized in a 0.9% saline solution and administered by endovenous injection at doses ranging between 0.5 and 5 mg/kg 30 minutes before capillary permeabilization.

Results

The extravasation induced by substance P is due to a dual activation mechanism of both the mast cells and the vasal endothelial cells, while the substance P fragment—peptide P6-11—causes extravasation only due to an effect on the endothelium through the interaction with the NK1 receptors ("Role of the N-terminal arginine in the histamine releasing activity of substance P, bradikinin and related peptides"; Deviller P., Drapeau G., Renoux M., Regoli D., Europ. J. Pharmacol. 168 (1989): 53-60.).

All the tested compounds significantly reduce the capillary permeability induced by the peptide P6-11 (Tables 7 and 8), while not significantly affecting the permeability induced by substance P (SP) (Table 9).

In particular, the potassium salt of GPI of Example 4a limits the extravasation induced by the substance P fragment P6-11.

Table 7 The compounds coded 4a, 2, and 6 at a sufficient dose limit the extravasation induced by P6-11.

| | Treatment | Absorbance |
|---|---|---|
| Group 1 | Saline + vehicle | 0.058 ± 0.009 |
| Group 2 | P 6-11 + vehicle | 0.108 ± 0.014* |
| Group 3 | P 6-11 + Ex. 4a 5 mg/kg | 0.081 ± 0.027 |
| Group 4 | P 6-11 + Ex. 2 5 mg/Kg | 0.092 ± 0.021 |
| Group 5 | P 6-11 + Ex. 2 10 mg/Kg | 0.079 ± 0.022• |
| Group 6 | P 6-11 + Ex. 6 5 mg/Kg | 0.131 ± 0.022 |
| Group 7 | P 6-11 + Ex. 6 10 mg/Kg | 0.072 ± 0.010• |

Student-Newman-Keuls Test *$p<0.05$ vs Group 1; •$p<0.05$ vs Group 2; $p<0.05$ vs Group 6.

TABLE 8

Dose dependent effect of compound coded Example 4a, on the extravasation induced by the P 6-11.

| | Treatment | Absorbance x10$^{-2}$ |
|---|---|---|
| Group 1 | P 6-11 + vehicle | 74 ± 3* |
| Group 2 | P 6-11 + Es 4a 0.5 mg/kg | 54 ± 4* |
| Group 3 | P 6-11 + Es 4a 1.5 mg/Kg | 57 ± 7* |
| Group 4 | P 6-11 + Es. 4a 5 mg/Kg | 34 ± 8* |

Student-Newman-Keuls Test *$p<0.05$.

Table 9 L-α-glycero-phospho-D-mio-inositol choline salt (Ex. 5) and L-α-glycero-phospho-D-mio-inositol lysine salt (Ex 6) on the extravasation induced by substance P

| Treatment | Absorbance |
|---|---|
| saline + vehicle | 0.126 ± 0.012 |
| substance P + vehicle | 0.278 ± 0.023 |
| substance P + Ex. 5 5 mg/kg | 0.222 ± 0.010 |
| substance P + Ex. 6 5 mg/Kg | 0.239 ± 0.015 |

The reported evidences show that the compounds of the invention limit the plasma protein extravasation induced by the terminal peptide of substance P, P6-11. The peptide P6-11 induces a protein extravasation through the epithelium according to a specific mechanism mediated by the neurokin receptor termed NK1. It must be recalled that the NK1, NK2, and NK3 receptors mediate the signal of the endogenous ligands SP, NKA, and NKB respectively, all of which recognize the terminal portion of SP present to the peptide P6-11.

In conclusion, the tested compounds of the invention are capable to negatively modulate the cPLA2 and thus to limit the cascade of events related to the arachidonic acid metabolism. The compounds of the invention are furthermore capable to limit the activation of the cPLA2 and the increase of arachidonic acid levels present in situations of altered barrier permeability such as the vasal-perineurium of the peripheral nervous system and the blood-brain barrier of the central nervous system induced by various stimuli, for example ATP.

The compounds of the invention modulate also the activation of the cPLA2 mediated by the bombesin receptors, which is involved in the disregulation of food intake and may thus be helpfully used for the treatment of pathologies mediated by such a cachexia mechanism, for example bulimia, anorexia, obesity and cachexia.

The compounds of the invention are furthermore capable to modulate the stimulation of the NK-1 receptor of an in vivo model.

The compounds of the invention can thus be a valid therapeutic tool for the treatment of pathologies mediated by an activation or over stimulation of the cPLA2, as those previously listed.

The dosages, timing and the ways of administration will be chosen according to the type, stage, seriousness and district of appearance of the pathology or alteration or of the eventual application in human or veterinarian health care and comprised between 0.1 and 100 mg/kg for 3-90 days for each therapy cycle. For all the pathologies mentioned are indicated the systemic, parenteral, oral and rectal administration, but also topic, transdermic and in any case such that to achieve the highest availability of the active substance. For oral formulations are privileged administrations as tablets, sugar coated tablets and capsules, but also powders and solutions/suspensions including nebulization.

For topic treatments are preferred gels, creams and solutions compatible with skin and mucosal use, including the gingival mucosa, together with eye drops for the administration into the conjunctival sac.

The injectable forms are formulated with solvents compatible for pharmaceutical use and for the endovenous, intramuscular and subcutaneous administration.

The same active compounds can be formulated at the proper concentrations, as supplements for oral intake for the prevention or coadiuvant treatment of alterations related to disreactive conditions in man and veterinarian medicine.

The following are some examples of pharmaceutical and cosmetic preparations which have only a descriptive, but not limitative purpose.

| Example A - Tablet | | |
|---|---|---|
| Active principle | Example 6 | 100 mg |
| Excipients | Microcrystalline cellulose | 160 mg |
| | Starch | 28 mg |
| | Lactose | 100 mg |
| | Stearic acid | 6.0 mg |
| Example B - injectable formulation | | |
| Vial 1 | | |
| Active principle | Example 4 lyophilised | 50 mg |
| Vial 2 | | |
| Excipient | Sodium phosphate bibasic12H2O | 12 mg |
| | Sodium phosphate monobasic 2 H2O | 1 mg |
| | Sodium chloride | 32 mg |
| | Water for injection | to 4 ml |
| Example C - cream W/O for topic application % mg | | |
| Active principle | Example 7 | 2 |
| Excipients | Twin 60 | 0.5 |
| | Polwax | 2.5 |
| | Cetylstearyl alcohol | 2 |
| | Carbomer | 0.5 |
| | TEA | 0.5 |
| | Glycerin | 3 |
| | Preservants | 1 |
| | Water | to 100 mg |

The invention claimed is:

1. Method of treatment of inflammation comprising the administration, to a patient in need thereof, of a compound of formula (I):

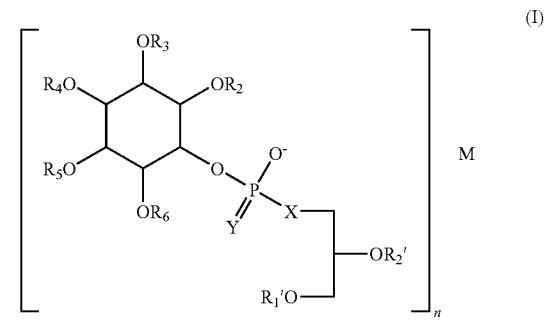

wherein:
R1', R2', R2, R3, R4, R5, R6 is each, independently,
(a) H; or
(b) C(O)A, an acylic mono-carboxylic acid or di-carboxylic acid, where A is a radical selected from the group consisting of
  (i) a saturated or unsaturated, straight or branched, alkyl radical having from 1 to no more than 8 carbon atoms and from 0 to no more than 4 double bonds;
  (ii) a mono- or polycyclic alkyl or alkenyl radical and
  (iii) an aryl, arylalkyl or heterocyclic radical having one or more heteroatoms;
wherein said radical is unsubstituted or substituted with one or more groups selected from the group consisting of keto, hydroxyl, acylamidic, halogen, mercapto, alkylthio or alkyldithio, —COOH, wherein the —COOH is salified to form a —COOM salt, or unsalified, and wherein M is the cation of a pharmaceutically acceptable inorganic element or a cation of a pharmacologically acceptable organic base, both having a valence n+, wherein n is 1 or 2 or 3, and;

X and Y are O.

2. A method according to claim 1, wherein M is:
(a) a biologically acceptable inorganic cation; or,
(b) a biologically acceptable organic cation having valence n+ wherein n is 1, 2, or 3.

3. A method according to claim 1, wherein:
(a) A is selected from the group consisting of
(i) a mono- or polycyclic alkyl or alkenyl radical having 5 to 30 carbon atoms; and,
(ii) an aryl radical, arylalkyl radical, or heterocycle radical having one or more heteroatoms and 4 to 15 carbon atoms, said one or more heteroatoms selected from the group consisting of N, O, and S.

4. A method according to claim 2, wherein M is:
(a) a biologically acceptable inorganic cation selected from the group consisting of chromium, copper, alkaline elements, earth alkaline, Zn and Fe; or,
(b) a cation of a biologically acceptable organic base selected from the group consisting of mono-, di-, tri-, and tetra-alkylammonium; N-(2-hydroxyethyl)dimethylammonium; choline cation; and an aminoacid cation selected from the group consisting of lysine, arginine, carnosine, dipeptides, tripeptides, and cations of xanthine base.

5. A method according to claim 1, wherein the inflammation is associated with a pathology mediated by activation or overstimulation of cPLA2, said pathology being associated with overstimulation of growth factors EGF or NGF and/or NK-1 receptor and/or of receptors coupled with G proteins that activate cPLA2, such as ATP receptors and/or bombesin receptors.

6. A method according to claim 1, wherein the inflammation is associated with a pathology mediated by activation or overstimulation of cPLA2, said pathology being cardiogenic or septic shock or viral or bacterial infection.

7. A method according to claim 1, wherein the inflammation is associated with a pathology mediated by activation or overstimulation of cPLA2, said pathology being a pathology of the respiratory apparatus resulting from acute pulmonary damage in an adult, a child, or a newborn infant or a chronic obstructive alteration.

8. A method according to claim 1, wherein the inflammation is associated with a pathology mediated by activation or overstimulation of cPLA2, said pathology being a dermatologic pathology selected from the group consisting of psoriasis, seborrhoic dermatitis, atopic dermatitis, and skin disreactivity from oxidative stress following UVB damage; or an ophthalmic pathology selected from the group consisting of glaucoma and conjunctivitis.

9. A method according to claim 1, wherein the inflammation is associated with a pathology mediated by activation or overstimulation of cPLA2, said pathology being a tumour pathology of the prostate or kidney.

10. A method according to claim 1, wherein the inflammation is associated with a pathology mediated by activation or overstimulation of cPLA2, said pathology being selected from the group consisting of alterations of gingival tissue due to a bacterial infection, and mucosal damage in intestinal ischaemia.

11. A method according to claim 1, wherein the inflammation is associated with a pathology mediated by activation or overstimulation of cPLA2, said pathology being an articular alteration selected from the group consisting of arthritis and arthrosis.

12. A method according to claim 1, wherein the inflammation is associated with a pathology mediated by activation or overstimulation of cPLA2, said pathology being selected from the group consisting of migraine, headache, pain, and hyperalgesia.

13. A method according to claim 1, wherein the inflammation is associated with a pathology mediated by activation or overstimulation of cPLA2, said pathology being selected from the group consisting of a cardiac disorder and cardiovascular disease associated with vascular remodelling.

14. A method according to claim 1, wherein the inflammation is associated with a pathology mediated by activation or overstimulation of cPLA2, said pathology being a pathology of the peripheral nervous system; a toxic-dismetabolic neuropathy; a pathology of the central nervous system selected from the group consisting of Alzheimer's disease, schizophrenia, and depression; a pathology caused by iatrogenic damage; a pathology caused by toxic agents such as cocaine; or a cutaneous disorder or alteration associated with the sphyngomielin cycle selected from the group consisting of the Hermansky-Pudlak syndrome and the Nieman-Pick syndrome.

15. A method according to claim 1, wherein the inflammation is associated with a pathology mediated by activation or overstimulation of cPLA2, said pathology being associated with damage to a vessel/nervous-system barrier such as the blood brain barrier, including pathologies associated with vessel/nervous-system barrier damage selected from the group consisting of neuronal edema, stroke, cerebral edema and hemorrhage, and transient ischemic attack.

16. A method according to claim 1, wherein the inflammation is associated with a pathology mediated by activation or overstimulation of cPLA2, said pathology being related to food intake disorders selected from the group consisting of bulimia, anorexia, cachexia, and obesity.

17. A method according to claim 1, wherein the inflammation is associated with a pathology mediated by activation or overstimulation of cPLA2, said pathology being a dis-metabolic pathology selected from the group consisting of diabetes and pancreatitis.

18. A method according to claim 1, wherein the compound of formula (I) is administered as an active ingredient in a veterinary pharmaceutical composition.

19. A method according to claim 1, wherein the compound of formula (I) is administered to the patient in one or more cycles of treatment, each treatment cycle comprising administering a dose of the compound of formula (I) included between 0.1 to 100 mg/kg for 3-90 days.

* * * * *